United States Patent

Gittos et al.

[11] Patent Number: 4,461,771
[45] Date of Patent: Jul. 24, 1984

[54] TREATMENT OF MIGRAINE WITH DIOXOPIPERIDINE DERIVATIVES

[76] Inventors: Maurice W. Gittos, 16 Rue Andre Malraux, Plobsheim Illkirch-Graffenstaden 67400, France; David A. Amey, 40 S. Rd., Luton, Bedfordshire LU1 3UD, England

[21] Appl. No.: 471,099

[22] Filed: Mar. 1, 1983

[51] Int. Cl.³ .......................................... A61V 31/445
[52] U.S. Cl. ................................................... 424/267
[58] Field of Search ......................................... 424/267

[56] References Cited

U.S. PATENT DOCUMENTS 3,963,729  6/1976  Gittos et al. ..................... 424/267

Primary Examiner—Stanley J. Friedman
Attorney, Agent, or Firm—William A. Drucker

[57] ABSTRACT

Migraine is treated with a 3-phenyl-3-aminoalkyl-4,4-dimethyl-2,6-dioxopiperidine derivative of the following general Formula I:

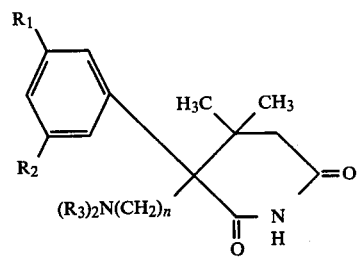

wherein:
$R_1$ represents methoxy, ethoxy and hydroxy;
$R_2$ represents methoxy, ethoxy, hydroxy or hydrogen, each $R_3$ independently represents methyl or ethyl; and
n represents 2 or 3, or a pharmaceutically acceptable acid addition salt thereof.

9 Claims, No Drawings

TREATMENT OF MIGRAINE WITH DIOXOPIPERIDINE DERIVATIVES

FIELD OF THE INVENTION

The invention relates to the prophylactic treatment of migraine with certain 3-phenyl-3-aminoalkyl-4,4-dimethyl-2,6-dioxopiperidines and provides a method of prophylactic treatment of migraine using said compounds.

BACKGROUND OF THE INVENTION

It is believed that 5-hydroxytryptamine (5-HT) is the naturally occurring substance most likely to play a role in the pathophysiology of migraine. Increased amounts of 5-HT and its metabolite 5-hydroxyindole acetic acid are excreted in the urine during most attacks. Further, plasma and platelet 5-HT concentrations fall rapidly at the onset of an attack and remain low whilst the headache persists. Moreover, attacks of migraine have been clearly associated with periods of thrombocytopaenia in certain patients. It has been proposed that compounds which block the activity of 5-HT would be of use in the treatment of migraine (J. R. Fozard, International Headache Congress 1980) reported in Advances in Neurology, Vol. 33, Raven Press, New York 1982).

The known migraine propylactic drugs methysergide, propranolol, amitriptyline, and chlorpromazine have widely different pharmacological activities but are all 5-HT D-receptor antagonists at the doses used clinically for the treatment of migraine and all reduce 5-HT transmission.

The reduction of 5-HT transmission also can be produced by the blockade of the enzyme tryptophan hydroxylase, the initial step in 5-HT biosynthesis and a known tryptophan hydroxylase inhibitor, para-chlorophenylalanine, has been shown to be beneficial in the treatment of migraine (F. Sicuteri, Headache 10, 124(1970)). However, the continued use of para-chlorophenylalanine in the treatment of migraine has been precluded because of its untoward toxic effects.

It is an object of the present invention to provide compounds which will reduce the activity of tryptophan hydroxylase by blocking the depolarization-induced induction of the enzyme. It is believed that the blockade of the induction of the enzyme diminishes the functional pool of 5-HT and thereby reduces 5-HT transmission and hence reduces, or eliminates, migraine attacks.

It has been disclosed in U.S. Pat. No. 3,963,729, of which we are the Inventors, that inter alia compounds of the following Formula I have central nervous system, especially antidepressant, activity:

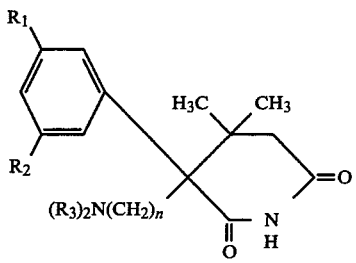

wherein:
$R_1$ represents methoxy, ethoxy or hydroxy;
$R_2$ represents methoxy, ethoxy, hydroxy or hydrogen;
each $R_3$ independently represents methyl or ethyl; and
n represents 2 or 3.

The specific examples of compounds of Formula I stated in the U.S. patent are 3-(3'-methoxyphenyl)-3-(3''-N,N-dimethylaminopropyl)-4,4-dimethyl-2,6-dioxopiperidine and 3-(3'-methoxyphenyl)-3-(2''-N,N-dimethyl aminoethyl)-4,4-dimethyl-2,6-dioxopiperidine.

It has now been found that the compounds of Formula I unexpectedly reduce the activity of tryptophan hydroxylase by blocking the depolarization induced induction of the enzyme and hence are of potential use in the prophylactic treatment of migraine.

SUMMARY OF THE INVENTION

According to the present invention, there is provided a method of prophylaxis of migraine which comprises administering to a patient at risk of migraine, an effective migraine-prophylactic amount of compound of the following general Formula I:

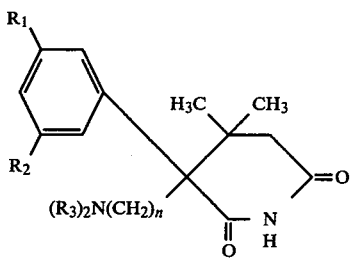

wherein:
$R_1$ represents methoxy, ethoxy or hydroxy;
$R_2$ represents methoxy, ethoxy, hydroxy or hydrogen; each $R_3$ independently represents methyl or ethyl; and
n represents 2 or 3, or a pharmacologically acceptable acid addition salt thereof.

Said amount usually will be in the range 0.01 mg/kg to 10 mg/kg, especially 0.1 mg/kg to 3 mg/kg.

DETAILED DESCRIPTION OF THE INVENTION

The compounds of general Formula I have the phenyl moiety substituted in one or both meta positions by methoxy, ethoxy, or hydroxy. It is presently preferred that the substituent(s) should be methoxy or hydroxy. It is also preferred that there should be only one substituent and that when there are two substituents they should be the same.

The amino group of the compound of Formula I is dimethylamino, diethylamino or methylethylamino with dimethylamino being presently preferred. The amino group is connected to the piperidine ring by a divalent ethylene (i.e. n=2) or trimethylene (i.e. n=3) radical with trimethylene being presently preferred.

Examples of compounds of Formula I include the following:
3-(3'-methoxyphenyl)-3-(2''-N,N-dimethylaminoethyl)-4,4-dimethyl-2,6-dioxopiperidine;
3-(3'-methoxyphenyl)-3-(3''-N,N-dimethylaminopropyl)-4,4-dimethyl-2,6-dioxopiperidine;
3-(3'-methoxyphenyl)-3-(2''-N,N-diethylaminoethyl)-4,4-dimethyl-2,6-dioxopiperidine;

3-(3'-methoxyphenyl)-3-(3"-N,N-diethylaminopropyl)-4,4-dimethyl-2,6-dioxopiperidine;
3-(3'-methoxyphenyl)-3-(2"-N-methyl-N-ethyl-aminoethyl)-4,4-dimethyl-2,6-dioxopiperidine;
3-(3'-methoxyphenyl)-3-(3"-N-methyl-N-ethyl-aminopropyl)-4,4-dimethyl-2,6-dioxopiperidine;
3-(3'-hydroxyphenyl)-3-(2"-N,N-dimethylaminoethyl)-4,4-dimethyl-2,6-dioxopiperidine;
3-(3'-hydroxyphenyl)-3-(3"-N,N-dimethylaminopropyl)-4,4-dimethyl-2,6-dioxopiperidine;
3-(3'-hydroxyphenyl)-3-(2"-N,N-diethylaminoethyl)-4,4-dimethyl-2,6-dioxopiperidine;
3-(3'-hydroxyphenyl)-3-(3"-N,N-diethylaminopropyl)-4,4-dimethyl-2,6-dioxopiperidine;
3-(3'-hydroxyphenyl)-3-(2"-N-methyl-N-ethyl-aminoethyl)-4,4-dimethyl-2,6-dioxopiperidine;
3-(3'-hydroxyphenyl)-3-(3"-N-methyl-N-ethyl-aminopropyl)-4,4-dimethyl-2,6-dioxopiperidine;
3-(3'-ethoxyphenyl)-3-(3"-N,N-dimethylaminopropyl)-4,4-dimethyl-2,6-dioxopiperidine;
3-(3'-ethoxyphenyl)-3-(3"-N,N-diethylaminopropyl)-4,4-dimethyl-2,6-dioxopiperidine;
3-(3',5'-dimethoxyphenyl)-3-(3"-N,N-dimethylaminopropyl)-4,4-dimethyl-2,6-dioxopiperidine;
3-(3',5'-dihydroxy)-3-(3"-N,N-dimethylaminopropyl)-4,4-dimethyl-2,6-dioxopiperidine;
3-(3',5'-diethoxy)-3-(3"-N,N-dimethylaminopropyl)-4,4-dimethyl-2,6-dioxopiperidine;

The compounds of Formula I block the depolarization induction of tryptophan hydroxylase thereby reducing the functional pool of 5-hydroxy tryptamine (5-HT), an action which, as explained above, will prevent or at least reduce the symptoms of migraine. Accordingly, the compounds of Formula I and their pharmacologically acceptable acid addition salts are useful in the treatment of migraine when administered in amounts sufficient to effective block the depolarisation induction of tryptophan hydroxylase.

The activity of the compounds as inhibitors of the depolarisation induction of tryptophan hydroxylase can be assessed by determining the $IC_{50}$ in rat brainstem slices as described by Margaret C. Boadle-Biber, Biochemical Pharmacology 27 1069 (1978). The $IC_{50}$ values are derived from concentration response curves as the concentration causing 50 percent inhibition of the depolarisation induction at 37° C. As an illustration the $IC_{50}$ of d,l 3-(3'-methoxyphenyl)-3-(3"-N,N-dimethylaminopropyl)-4,4-dimethyl-2,6-dioxopiperidine hydrochloride is 10 μM.

The activity of the compounds to reduce 5-HT transmission can be assessed in vivo by measuring their effect on the hyperthermia induced by an intraperitoneal injection of fenfluramine (see A. Sulpizio et al, Life Sciences 22 1439 (1978). As an illustration a four day chronic pretreatment of rats with 3-(3'-methoxyphenyl)-3-(3"-N,N dimethylaminopropyl) 4,4-dimethyl-2,6-dioxopiperidine hydrochloride at a dose level of 10 mg/kg ip. twice daily produced a 50 percent reduction in the hyperthermia induced by fenfluramine administered at a dose level of 7.5 mg/kg ip.

The compounds of Formula I can be administered in various manners to achieve the desired effect. The compounds can be administered alone or in the form of pharmaceutical preparations to the patient being treated either orally or parenterally, for example subcutaneously or intravenously. The amount of compound administered will vary and can be any effective migraine relieving amount. Depending upon the patient and the mode of administration, the quantity of compound administered may vary over a wide range to provide from about 0.01 mg/kg to 10 mg/kg, usually 0.1 mg/kg to 3 mg/kg, of body weight of the patient per dose. Unit doses of these compounds can contain, for example from about 0.1 mg to 200 mg usually 1 to 100 mg and preferably 10 to 100 mg of the compound and may be administered, for example from 1 to 4 times daily.

The term "unit dosage form" is used herein to mean a single or multiple dose form containing a quantity of the active ingredient in admixture with or otherwise in association with the diluent or carrier, said quantity being such that one or more predetermined units are normally required for a single therapeutic administration. In the case of multiple dose forms such as liquids or scored tablets, said predetermined unit will be one fractin, such as a 5 ml (teaspoon) quantity of a liquid or a half or quarter of a scored tablet, of the multiple dose form.

The pharmaceutical formulations in which form the active compounds of the invention will normally be utilized are prepared in a manner well known per se in the pharmaceutical art and usually comprise at least one active compound of the invention in admixture or otherwise in association with a pharmaceutically acceptable carrier or diluent therefor. For making those formulations the active ingredient will usually be mixed with a carrier, or diluted by a diluent, or enclosed or encapsulated in a capsule, sachet, cachet, paper or other container. A carrier or diluent may be solid, semi-solid or liquid material which serves as a vehicle, excipient or medium for the active ingredient. Suitable carriers or diluents are well known per se.

The formulations may be adapted for enteral or parenteral use and may be administered to the patient in the form of tablets, capsules, suppositories, solutions, suspensions or the like.

In the specific examples included hereinbelow illustrative examples of suitable pharmaceutical formulations are described.

The compounds of general Formula I wherein $R_1$ and/or $R_2$ represent methoxy or ethoxy can be prepared by treating in manner known per se, as disclosed in U.S. Pat. No. 3,963,729, the corresponding alkyl ester of 4-dialkylaminoalkyl-4-cyano-4-(alkoxyphenyl)-3,3-dimethylbutanoic acid of the following general Formula 2 with an acid condensing agent:

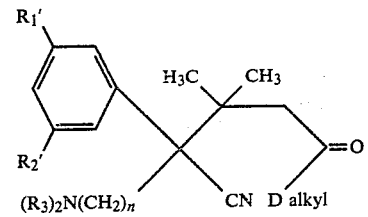

wherein D represents sulphur or, more usually, oxygen, $R'_1$ represents methoxy or ethoxy, $R'_2$ represents methoxy, ethoxy or hydrogen, and $R_3$ and n are as defined in connection with Formula I.

The acid condensing agent preferably is a Bronsted acid, for example sulphuric or, more preferbly, hydrochloric acid in the presence of a nucleophile for example water or acetic acid, and the reaction is carried out at an elevated temperature, advantageously in the range 60° to 120° C. for a period of 1 to 30 hours. If a volatile acid like hydrochloric acid is used the mixture can be evaporated under reduced pressure and the residue crystallised from a suitable solvent, for example water or ethanol, to give the acid addition salt of the desired dioxopiperidine derivative. Alternatively, or if a non-volatile acid is used, the cooled mixture can be neutralised with a weak base, for example ammonium hydroxide, to a pH in the range of 7.5 to 9.5. Said neutralisation is strongly exothermic and accordingly advantageously is carried out with cooling to a temperature in the range of 0° to 30° C. The desired dioxopiperidine derivative can be isolated by filtration or by extraction into a suitable solvent for example chloroform or methylene chloride and subsequent recovery from the solvent.

The compounds of the general Formula I where $R_1$ and/or $R_2$ represent hydroxy can be prepared by treating in manner known per se the corresponding alkoxy compound of general Formula I wherein $R_1$ and/or $R_2$ represents methoxy or ethoxy with an acid dealkylating agent, for example hydrobromic acid or boron tribromide. The dealkylation is performed at a suitable temperature depending on the known reactivity of the reagent, for example at 100°–120° C. for hydrobromic acid and −40° to +10° C. for boron tribromide, and the reaction is carried out for a period of from 1 to 4 hours. The required hydroxyphenyl dioxopiperidine derivative is isolated from the mixture by dilution with water and then neutralisation as for the alkoxyphenyl dioxopiperidines above.

Alternatively, the compounds of general Formula I wherein $R_1$ and/or $R_2$ represent hydroxy can be prepared directly by treating the corresponding alkyl ester of 4-dialkylaminoalkyl-4-cyano-4-alkoxyphenyl-3,3 dimethylbutanoic acid of Formula 2 with an acid dealkylation condensing agent for example hydrobromic or hydri-iodic acid.

As mentioned previously, the compounds of Formula I can be used in the form of their pharmacologically acceptable acid addition salts.

The pharmacologically acceptable acid addition salts can be non-toxic addition salts with suitable acids, such as those with inorganic acids, for example hydrochloric, hydrobromic, nitric, sulfuric or phosphoric acids, or with organic acids, such as organic carboxylic acids, for example, glycollic, maleic, hydroxymaleic, malic, tartaric, citric, salicyclic, o-acetyloxybenzoic, nicotinic or isonicotinic, or organic sulphonic acids, for example methane sulphonic, ethane sulphonic, 2-hydroxyethane sulphonic, toluene-p-sulphonic, or naphthalene-2-sulphonic acids.

An acid addition salt may be converted into the free compound according to known methods, for example, by treating it with a base, such as with a metal hydroxide or alkoxide, for example an alkali or alkaline earth metal hydroxide, for example, lithium hydroxide, sodium hydroxide, potassium hydroxide or calcium hydroxide; with a metal carbonate, such as an alkali metal or an alkaline earth metal carbonate or hydrogen carbonate, for example, sodium, potassium or calcium carbonate or hydrogen carbonate; with trialkylamine; or with an anion exchange resin.

The invention is illustrated in the following non-limiting Examples.

EXAMPLE 1

3-(3′-Methoxyphenyl-3-(3″-N,N-dimethylaminopropyl)-4,4-dimethyl-2,6-dioxopiperidine hydrochloride A solution of ethyl 4-(3′-N,N-dimethylaminopropyl)-4-cyano-4-(3″-methoxyphenyl)-3,3 dimethylbutanoate (29.8 g) in the 2.5N Hcl (100 ml) is refluxed for 3.5 hours and cooled to room temperature to give crystals of 3-(3′-methoxyphenyl)-3-(3″-N,N-dimethylaminopropyl)-4,4-dimethyl-2,6-dioxopiperidine hydrochloride m.p. 290° C. (21 g). It is recrystallised from ethanol.

EXAMPLE 2

3-(3′,5′-Dimethoxyphenyl)-3-(3″-N,N-dimethylaminopropyl)-4,4-dimethyl-2,6-dioxopiperidine A solution of ethyl 4-(3′-N,N-dimethylaminopropyl)-4-cyano-4-(3″,5″-dimethoxyphenyl)-3,3-dimethylbutanoate (4.2 g) in 5N hydrochloric acid (25 ml) is refluxed for 2 hours, the mixture evaporated and the residue treated with dilute ammonium hydroxide. The precipitated oil is extracted with chloroform and the dried (MgSO₄) chloroform solution evaporated. Crystallisation of the residue from aqueous methanol gives 3-(3′,5′-dimethoxyphenyl)-3-(3″-N,N-dimethylaminopropyl)-4,4-dimethyl-2,6-dioxopiperidine (2.1 g) m.p. 174°–5° C.

EXAMPLE 3

3(3′-Methoxyphenyl)-3-(2″-N,N-dimethylaminoethyl)-4,4-dimethyl-2,6-dioxopiperidine A solution of ethyl 4-(2′-N,N-dimethylaminoethyl)-4-cyano-4-(3″-methoxyphenyl)-3,3-dimethylbutanoate (30 g) in a mixture of glacial acetic acid (30 ml) and concentrated sulphuric acid (30 ml) is heated at 100° C. for 2 hours, cooled and poured into a mixture of crushed ice and concentrated ammonium hydroxide. The pH of the mixture is adjusted to 8 before being extracted with methylene chloride. Evaporation of the dried methylene chloride solution gives a residue which solidifies on treatment with aqueous methanol. Recrystallisation from aqueous methanol gives 3-(3′-methoxyphenyl)-3-(2″-N,N-dimethylaminoethyl)-4,4-dimethyl-2,6 dioxopiperidine (16.5 g) m.p. 205°–6° C.

EXAMPLE 4

3-(3′-Hydroxyphenyl)-3-(3″-N,N-dimethylaminopropyl)-4,4 dimethyl-2,6-dioxopiperidine A solution of ethyl 4-(3′-N,N-dimethylaminopropyl) 4-cyano-4-(3″-methoxyphenyl)-3,3-dimethylbutanoate (12 g) in 48% hydrobromic acid is refluxed for 4 hours and evaporated to dryness under reduced pressure. A solution of the residue in water is treated with dilute ammonium hydroxide until the pH of the mixture is 7.7 and the oil extracted with chloroform. Evaporation of the dried (MgSO₄) chloroform solution affords a residue which forms crystals of 3-(3′-hydroxyphenyl)-3-(3″-N,N-dimethylaminopropyl)-4,4-dimethyl-2,6-dioxopiperidine (6.4 g) m.p. 242–3° C. on crystallisation from aqueous methanol.

EXAMPLE 5

Tablets each having the following composition were made up as follows.

|     |                                                                                           | mg per tablet |
| --- | ----------------------------------------------------------------------------------------- | ------------- |
| (a) | 3(3'-methoxyphenyl)-3-(3''-N,N—dimethylaminopropyl)-4,4-dimethyl-2,6-dioxopiperidine hydrochloride | 50            |
| (b) | Lactose                                                                                   | 51.5          |
| (c) | Maise starch dried                                                                        | 45            |
| (d) | magnesium stearate                                                                        | 1.5           |

EXAMPLE 6

|     |                                                                          | mg/suppository |
| --- | ------------------------------------------------------------------------ | -------------- |
| (a) | 3(3'-Hydroxyphenyl)-3-(3''-N,N—dimethylaminopropyl)-4,4-dimethyl-2,6-dioxopiperidine | 20             |
| (b) | Oil of Theobroma (cocoa butter)                                          | 980            |

The compound (a) is powdered and passed through a BS No. 100 sieve and triturated with molten oil of Theobroma at 45° C. to form a smooth suspension. The mixture is well stirred and poured into moulds each of nominal 1 G capacity to produce suppositories.

We claim:

1. A method of prophylaxis of migraine which comprises administering to a patient suffering from migraine, an effective migraine-prophylactic amount of a compound of the following general Formula I:

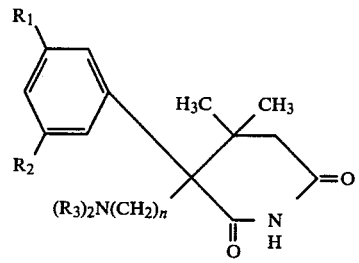

wherein:
$R_1$ represents methoxy, ethoxy and hydroxy;
$R_2$ represents methoxy, ethoxy, hydroxy or hydrogen,
each $R_3$ independently represents methyl or ethyl; and
n represents 2 or 3, or a pharmaceutically acceptable acid addition salt thereof.

2. A method as claimed in claim 1 wherein the said compound is administered in an amount of 0.01 mg/kg to 10 mg/kg.

3. A method as claimed in claim 2 wherein the said compound is administered in an amount of 0.1 mg/kg to 3 mg/kg.

4. A method as claimed in claim 1 wherein $R_1$ represents methoxy or hydroxy and $R_2$ represents methoxy, hydroxy or hydrogen.

5. A method as claimed in claim 1 wherein $R_2$ represents hydrogen.

6. A method as claimed in claim 1 wherein each $R_3$ represents methyl.

7. A method as claimed in claim 1 wherein n represents 3.

8. A method as claimed in claim 1 wherein $R_1$ is methoxy or hydroxy, $R_2$ is hydrogen, each $R_3$ is methyl and n is 3.

9. A method as claimed in claim 1 wherein the compound is 3-(3'-methoxyphenyl)-3-(3''-N,N-dimethylamino) 2,6-dioxopiperidine.

* * * * *